(12) United States Patent
Petersson et al.

(10) Patent No.: US 7,346,384 B2
(45) Date of Patent: Mar. 18, 2008

(54) METHOD OF MAGNETIC RESONANCE INVESTIGATION OF A SAMPLE USING A NUCLEAR SPIN POLARISED MR IMAGING AGENT

(75) Inventors: Stefan Petersson, Malmo (SE); Oskar Axelsson, Malmo (SE); Haukur Johanneson, Malmo (SE)

(73) Assignee: GE Healthcare AS, Oslo (NO)

(*) Notice: Subject to any disclaimer, the term of this patent is extended or adjusted under 35 U.S.C. 154(b) by 801 days.

(21) Appl. No.: 10/385,822

(22) Filed: Mar. 11, 2003

(65) Prior Publication Data

US 2003/0212323 A1 Nov. 13, 2003

Related U.S. Application Data

(63) Continuation of application No. PCT/GB01/04096, filed on Sep. 11, 2001.

(60) Provisional application No. 60/259,933, filed on Jan. 5, 2001.

(30) Foreign Application Priority Data

Sep. 12, 2000 (GB) ................................ 0022341.2

(51) Int. Cl.
*A61B 5/05* (2006.01)
(52) U.S. Cl. ...................... 600/420; 600/410; 600/431
(58) Field of Classification Search ................ 600/420, 600/431, 410
See application file for complete search history.

(56) References Cited

U.S. PATENT DOCUMENTS

| 4,612,185 A | * | 9/1986 | Dean .......................... 424/9.37 |
| 4,922,203 A |   | 5/1990 | Sillerud et al. ............. 324/307 |
| 5,283,525 A | * | 2/1994 | Lamerichs et al. ......... 324/307 |
| 5,539,315 A | * | 7/1996 | Cory et al. .................. 324/318 |
| 5,617,859 A | * | 4/1997 | Souza et al. ................ 600/420 |
| 5,707,875 A |   | 1/1998 | Tamura et al. .............. 436/173 |

FOREIGN PATENT DOCUMENTS

| DE | 4203254 | 8/1993 |
| WO | WO 97/37239 | 10/1997 |
| WO | WO 99/35508 | 7/1999 |
| WO | WO 00/40988 | 7/2000 |

* cited by examiner

*Primary Examiner*—Eleni Mantis Mercader
*Assistant Examiner*—Jacqueline Cheng
(74) *Attorney, Agent, or Firm*—Robert F. Chisholm

(57) ABSTRACT

The present invention provides a method of contrast enhanced magnetic resonance imaging of a sample, said method comprising: a) administering a hyperpolarised MR contrast agent comprising non-zero nuclear spin nuclei into said sample for fluid dynamic investigations of the vasculature, b) exposing said sample or part of the sample to radiation of a frequency selected to excite nuclear spin transitions in said non-zero nuclear spin nuclei, c) detecting MR signals from said sample using any suitable manipulation method including pulse sequences. The invention also provides novel compounds.

16 Claims, 1 Drawing Sheet

METHOD OF MAGNETIC RESONANCE INVESTIGATION OF A SAMPLE USING A NUCLEAR SPIN POLARISED MR IMAGING AGENT

This application claims priority from Continuation of PCT/GB01/04096 filed on Sep. 11, 2001, which claims priority from Provisional Application 60/259,933 filed on Jan. 5, 2001 and to United Kingdom Application No. 0022341.2 filed on Sep. 12, 2000 all of which are hereby incorporated by reference.

FIELD OF INVENTION

The present invention relates to methods of magnetic resonance imaging (MRI), in particular to a technique involving polarisation transfer between different nuclei with different gyromagnetic ratios (V).

BACKGROUND OF THE INVENTION

Magnetic resonance imaging is a diagnostic technique that has become particularly attractive to physicians as it is non-invasive and does not involve exposing the patient under study to potentially harmful radiation such as X-rays.

In order to achieve effective contrast between MR images of different tissue types, it has long been known to administer to the subject MR contrast agents (e.g. paramagnetic metal species) which affect relaxation times in the zones in which they are administered or at which they congregate. MR signal strength is dependent on the population difference between the nuclear spin states of the imaging nuclei. This is governed by a Boltzmann distribution and is dependent on temperature and magnetic field strength. Techniques have been developed which involve-ex vivo nuclear spin polarisation of agents containing non zero nuclear spin nuclei (e.g. $^3$He), prior to administration and MR signal measurement. Some such techniques involve the use of polarising agents, for example conventional OMRI contrast agents or hyperpolarised gases to achieve ex vivo nuclear spin polarisation of non zero nuclear spin nuclei in an administrable MR imaging agent. By polarising agent is meant any agent suitable for performing ex vivo polarisation of an MR imaging agent.

The ex vivo method has the advantage that it is possible to avoid administering the whole of, or substantially the whole of, the polarising agent to the sample under investigation, whilst still achieving the desired nuclear spin polarisation in the MR imaging agent. Thus the method is less constrained by physiological factors such as the constraints imposed by the administrability, biodegradability and toxicity of OMRI contrast agents in in vivo techniques.

MRI methods involving ex vivo nuclear spin polarisation may be improved by using nuclear.spin polarised MR imaging agents comprising in their molecular structure nuclei capable of emitting MR signals in a uniform magnetic field (e.g. MR imaging nuclei such as $^{13}$C or $^{15}$N nuclei) and capable of exhibiting a long $T_1$ relaxation time, and preferably additionally a long $T_2$ relaxation time. Such agents are referred to hereinafter as "high $T_1$ agents". A high $T_1$ agent, a term which does not include $^1$H$_2$O, will generally be water-soluble and have a $T_1$ value of at least 6 seconds in D$_2$O at 37° C. and at a field of 7T, preferably 8 secs or more, more preferably 10 secs or more, especially preferably 15 secs or more, more especially preferably 30 sees or more, yet more especially preferably 70 secs or more, even yet more especially preferably 100 secs or more. Unless the MR imaging nucleus is the naturally most abundant isotope, the molecules of a high $T_1$ agent will preferably contain the MR imaging nucleus in an amount greater than its natural isotopic abundance (i.e. the agent will be,enriched" with said nuclei).

The use of hyperpolarised MR contrast agents in MR investigations such as MR imaging has the advantage over conventional MR techniques in that the nuclear polarisation to which the MR signal strength is proportional is essentially independent of the magnetic field strength in the.MR apparatus. Currently the highest obtainable field strengths in MR imaging apparatus are about 8T, while clinical MR imaging apparatus are available with field strengths of about 0.2 to 1.5T. Since superconducting magnets and complex magnet construction are required for large cavity high field strength magnets, these are expensive. Using a hyperpolarised contrast agent, since the field strength is less critical it is possible to make images at all field strengths from earth field (40-50 μT) up to the highest achievable fields. However there are no particular advantages to using the very high field strengths where noise from the patient begins to dominate over electronic noise (generally at field strengths where the resonance frequency of the imaging nucleus is 1 to 20 MHz) and accordingly the use of hyperpolarised "contrast agents opens the possibility of high performance imaging using low cost, low field strength magnets.

As has been demonstrated previously (see for example the present Applicant's own earlier International Publication No. WO-A-99/35508, the disclosure of which is hereby incorporated by reference) it is possible to hyperpolarise compounds comprising long $T_1$ nuclei, e.g. $^{13}$C or $^{15}$N nuclei, in order to produce injectable contrast agents. For example, it is possible to use the 'para-hydrogen method'— see Applicant's own earlier International Publication No. WO-A-99/24080—or dynamic nuclear polarisation (DNP) see WO-A-99/35508.

one problem with these previously described techniques is that whilst the value of the gyromagnetic ratio, γ, for hydrogen is 42.6 MHz/T, it is much lower for both carbon and nitrogen, at 10.7 MHz/T and 4.3 MHz/T, respectively. However, the signal-to-noise ratio of images generated by MRI is, to a first approximation, linearly dependent on the value of the gyromagnetic ratio of the imaged nucleus. Therefore, assuming that the concentration of the contrast medium and the degree of polarisation are equal, images generated using a $^{13}$C or more especially a $^{15}$N-based contrast medium will have significantly lower signal-to-noise ratios than those images generated using a $^1$H-based contrast medium.

A further drawback in using $^{13}$C or $^{15}$N-based contrast medium, particularly in angiography, relates to the gradient power that is required for the MRI. This is due to the fact that the required gradient is inversely dependent upon the value of the gyromagnetic ratio of the imaged nucleus. Thus, in the case of $^{13}$C_ or $^{15}$N-based contrast media with relatively low gyromagnetic ratio values, correspondingly high gradients are required. Such inverse proportionality between gradient and the value of the gyromagnetic ratio of the imaged nucleus means $^{13}$C that -based imaging must be performed using gradients approximately four times that required for a given pulse sequence used in 'H-based imaging. Furthermore, when $^{15}$N-based imaging is required, the gradient needs to be approximately 10 times that required for $^1$H-based imaging.

At present, in $^1$H-based angiography, the maximum available gradient amplitudes are used in order to suppress phase artifacts.

Thus, if hyperpolarised contrast media containing nonproton imaging nuclei, particularly $^{13}C$ or $^{15}N$ nuclei, are to be used in combination with fast imaging sequences, there will be a less than optimal image quality, due to the lower values of the gyromagnetic ratio of the non-proton imaging nuclei.

Furthermore, a problem in using nuclei with relatively high gyromagnetic ratios in ex vivo polarisation techniques is that such nuclei have comparatively short $T_1$ values. Therefore, it is possible to alleviate such problems by employing nuclei with relatively low gyromagnetic ratios in the ex vivo polarisation step and utilising a pulse sequence to transfer polarisation from the nuclei with relatively low gyromagnetic ratios to nuclei with relatively high gyromagnetic ratios.

SUMMARY OF THE INVENTION

In view of the needs of the art, the present invention therefore provides a method of magnetic resonance investigation of a sample, preferably a human or non-human animal body. The method includes the steps of:
i) obtaining a MR imaging agent containing in its molecular structure at least one storage non-zero nuclear spin nuclei;
ii) nuclear spin polarising said storage nuclei in the MR imaging agent;
iii) administering the polarised MR imaging agent to the sample;
iv) subjecting the sample to a pulse sequence which causes polarisation to be transferred from the storage nuclei to at least one detection non-zero nuclear spin nuclei, wherein the gyromagnetic ratio of the detection nuclei is greater than that of the storage nuclei;
v) exposing the sample to a radiation at a frequency selected to excite nuclear spin transitions in selected detection nuclei therein;
vi) detecting magnetic resonance signals from the sample; and
vii) optionally generating an image, dynamic flow data, diffusion data, perfusion data, physiological data or metabolic data from the detected signals.

The present invention further provides a reporter compound containing at least two nonzero nuclear spin nuclei of different gyromagnetic ratio values preferably wherein the the at least two non-zero nuclear spin nuclei are separated by up to 5 chemical bonds.

DETAILED DESCRIPTION OF THE PREFERRED EMBODIMENTS OF THE INVENTION

Figure 1:
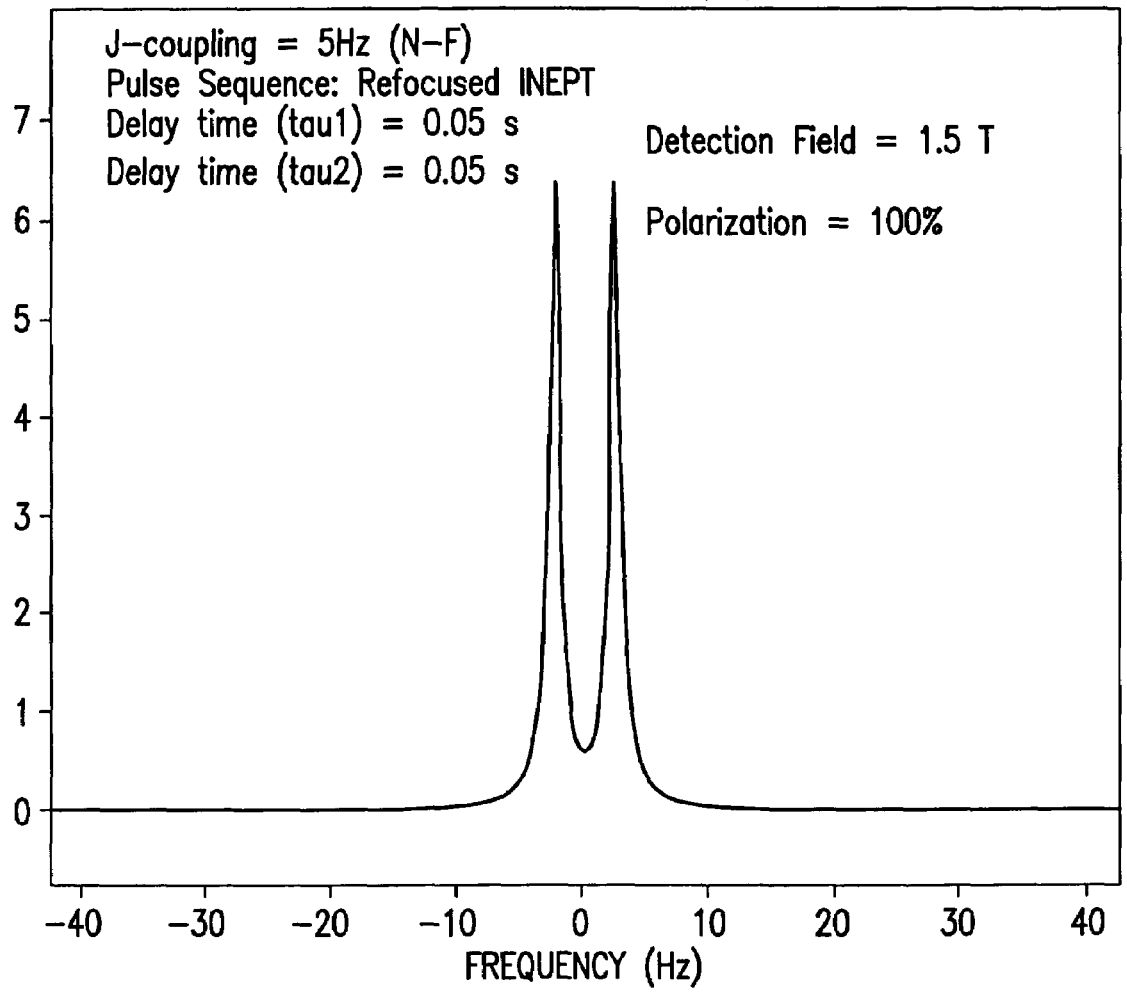
FIG. 1 shows a calculated $^{19}F$ spectrum from molecule (I).

The present invention thus relates in one aspect to a method whereby the above-mentioned drawbacks are addressed by using a technique in which after production of a contrast media containing hyperpolarised nuclei, preferably $^{13}C$ or $^{15}N$ nuclei, the media is injected into the patient, and the patient is then subjected to a pulse sequence which transfers polarisation from the hyperpolarised nuclei, e.g. the $^{13}C$ or $^{15}N$ nuclei, to nuclei having a higher value of the gyromagnetic ratio, e.g. $^1H$, $^{19}F$ or $^{31}P$ nuclei, which then serve as the imaging nuclei for image generation.

Thus viewed from one aspect the present invention provides a method of magnetic resonance investigation of a sample, preferably a human or non-human animal body (e.g. a mammalian, reptilian or avian body), said method comprising:
i) obtaining a MR imaging agent containing in its molecular structure at least one storage non-zero nuclear spin nuclei;
ii) nuclear spin polarising said storage nuclei in said MR imaging agent;
iii) administering the polarised MR imaging agent to said sample;
iv) subjecting said sample to a pulse sequence which causes polarisation to be transferred from said storage nuclei, e.g. $^{13}C$ or $^{15}N$ nuclei, to at least one detection non-zero nuclear spin nuclei, e.g. $^1H$, $^{19}F$ or $^{31}P$ nuclei, wherein the gyromagnetic ratio of said detection nuclei is greater than that of said storage nuclei;
v) exposing said sample to a radiation at a frequency selected to excite nuclear spin transitions in selected detection nuclei therein;
vi) detecting magnetic resonance signals from said sample; and
vii) optionally generating an image, dynamic flow data, diffusion data, perfusion data, physiological data (e.g. pH, $PO_2$, $pCO_2$, temperature or ionic concentrations) or metabolic data from said detected signals.

Preferably, the method of the invention is used for angiography. Also preferably, the method can be used for any fluid dynamic investigations of the vascular system, including perfusion etc. Preferably, the efficiency of the polarisation transfer described in step iv) above is to be-dependent on the pH, oxygen tension, temperature or some other physiological parameter, thus allowing maps of said parameters to be constructed via the methods of the present invention.

Thus the invention may involve the sequential steps of nuclear spin polarising (otherwise referred to herein as Ilhyperpolarisingll) a MR imaging agent containing in its molecular structure a non-zero nuclear spin nucleus, for example a $^3Li$, $^{13}C$, $^{15}N$, $^{29}Si$ or $^{77}Se$ nucleus, administering the hyperpolarised MR imaging agent (preferably in solution but optionally as a finely divided particulate, and preferably in the absence of a portion of, more preferably substantially the whole of, the species involving in transferring the polarisation to the MR imaging agent), subjecting the sample to a pulse sequence wherein polarisation is transferred from the hyperpolarised nuclei, for example $^3Li$, $^{13}C$, $^{15}N$, $^{29}Si$ or $^{77}Se$ nuclei, preferably $^{13}C$, $^{15}N$, $^{29}Si$ or $^{77}Se$ nuclei, more preferably $^{13}C$ or $^{15}N$ nuclei, to nuclei having a higher value of gyromagnetic ratio, preferably at least 25% higher, more preferably at least 50% higher, especially preferably at least 100% higher, most especially preferably at least ten times higher, for example $^1H$, $^{19}F$ or $^{31}P$ nuclei, preferably $^{19}F$ nuclei, with high efficiency, preferably at least 75% efficiency, more preferably at least 90%. efficiency and most preferably about 100% efficiency, and conventional in vivo MR signal generation and measurement. $^1H$ nuclei may be preferred however in certain situations, for example if the background signals are low. The MR signals obtained in this way may conveniently be converted by conventional manipulations into 2-, 3- or 4-dimensional data including flow, diffusion, physiological or metabolic data.

In the method of the invention the sample may be inanimate or animate, e. g. a human or animal, a cell culture, a membrane-free culture, a chemical reaction medium, etc. Thus, after the MR imaging agent has been polarised and administered, e.g. by injection into the patient, the initial excitation, often a 900 pulse in conventional MR techniques, of the imaging pulse sequence is replaced by a pulse train which has the effect of transferring the polarisation from the low gyromagnetic ratio nuclei to the high gyromagnetic ratio nuclei. By "pulse sequence" it is meant a sequence of pulses of electromagnetic radiation, e.g. rf pulses. Although there are several pulse sequences that can be used, merely by way of example, for polarisation transfer from $^{13}C$ to $^1H$ nuclei, one can use standard DEPT and INEPT/refocused INEPT pulse sequences, as commonly found in the standard literature, or any other improvements thereof. The sequence used for polarisation transfer is then followed by a conventional imaging sequence, for example a RARE sequence. Optionally a saturation sequence can be utilised prior to the polarisation transfer sequence in order to eliminate, or at least reduce, background signals, for example background proton signals.

It is possible to eliminate the background signal in conjunction with the present 'spin bank' technique. In order to achieve this, then before the polarisation transfer is performed, the background signal is saturated. Since the recovery time ($T_1$) of the background signal is much longer than the duration of the polarisation transfer sequence there is in principle no background signal present at the time of the main signal acquisition. In such cases, $^1H$ nuclei are preferred. Indeed, only when $^1H$ nuclei are used as the high gyromagnetic ratio nuclei is the saturation pulse required.

In the terminology of the present invention, the pulse sequence essentially effects a withdrawal from the spin bank where the polarisation was stored in the $^{13}C$ nuclei.

Although the 'spin bank can comprise polarisation stored in any suitable low gyromagnetic ratio nuclei, e.g. $^3Li$, $^{13}C$, $^{15}N$, $^{29}Si$ or $^{77}Se$, those with the lowest gyromagnetic ratios are most preferred, e.g. $^{13}C$ or $^{15}N$, most preferably $^{15}N$. As high gyromagnetic ratio nuclei, $^1H$, $^{19}F$ or $^{31}P$ nuclei can be used, preferably $^{19}F$ or $^{31}p$ nuclei, wherein the MR images thus produced are background-free.

Most particularly preferred as a combination would be $^{15}N$ as the 'storage' low gyromagnetic ratio nuclei and $^{19}F$ as the 'detection' high gyromagnetic ratio nuclei. This combination would have several advantages: very long $T_1$ times, high sensitivity, no natural background, and the resonance frequency of $^{19}F$ is close enough to $^1H$ so that only very minor modifications would be required to standard imaging machines, e.g. a conventional spectroscopy-adapted imager would suffice.

It is especially preferred that the low and high gyromagnetic ratio nuclei are both present within the same molecule, i.e. in molecules wherein the nuclei are connected via covalent bonds, and preferably the low and high gyromagnetic ratio nuclei are to be found at a separation of up to 5 bonds, more preferable 2 to 4 bonds, especially 3 bonds. Any intervening nuclei are preferably I=0 nuclei and in their normal isotopic occurrence and if substituted, are also preferably substituted by I≠½ nuclei, e.g. I=0 nuclei or deuterium nuclei, so as to avoid splitting the nuclear magnetic resonance frequency of the low and high gyromagnetic ratio nuclei. The MR imaging agent is preferably also a high $T_1$ agent (for the low gyromagnetic ratio nucleus) and also it is preferably water soluble.

The use of MR imaging agents such as those described above and some of the MR imaging agents themselves are novel and form further aspects of the present invention.

Viewed from a first of these aspects the invention provides a reporter compound containing at least two non-zero nuclear spin nuclei of different gyromagnetic ratio values preferably wherein the said at least two non-zero nuclear spin nuclei are separated by up to 5 chemical bonds, more preferably 2 to 4 chemical bonds, especially preferably 3 chemical bonds, and preferably wherein the said at least two non-zero nuclear spin nuclei are separated by atoms the most abundant isotope of which has a nuclear spin of I=O. More preferably, the gyromagnetic ratio of the high value nuclei is at least 25% higher, more preferably at least 50% higher, especially preferably at least 100% higher, most especially preferably at least ten times higher than the gyromagnetic ratio of the low value nuclei.

Especially preferably, the compounds are such that said atoms separating the said at least two non-zero nuclear spin nuclei are substituted only by I≠½ nuclei, e.g. I=0 nuclei.

In cases where there are at least two non-$^1H$ nuclei and $^1H$ nuclei in the reporter compound, then such compounds provide for the possibility of polarisation transfer from the lower gyromagnetic ratio value nuclei in the compound to either the $^1H$ nuclei or the higher gyromagnetic ratio value nuclei depending upon the particular pulse sequence chosen. In this way, for example with a $^{15}N$, $^{19}F$ and $^1H$ containing MR imaging agent, $^1H$ imaging may provide a locally enhanced Iseminative, image for comparison with a $^{19}F$ image which will pick-up essentially only the MR imaging agent's distribution.

Viewed from a further aspect the invention provides a physiologically tolerable MR imaging agent composition comprising an MR imaging agent together with one or more physiologically tolerable carriers or excipients, said imaging agent containing at least two non-zero nuclear spin nuclei of different gyromagnetic ratio values preferably wherein the said at least two non-zero nuclear spin nuclei are separated by up to 5 chemical bonds, more preferably 2 to 4 chemicals bonds, especially preferably 3 chemical bonds, and preferably wherein the said at least two non-zero nuclear spin nuclei are separated by atoms the most abundant isotope of which has a nuclear spin of I=O.

An example of a particularly preferred reporter compound for use in the method of the present invention is shown below:

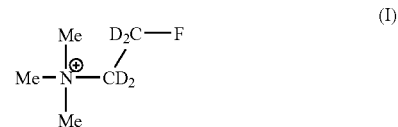

(I)

This molecule (I) contains the $^{15}N$-$^{19}F$ combination of nuclei noted to be particularly preferred. Furthermore, this molecule has a high $T_1$ value (of about 3 minutes), has good water solubility and a $^{15}N$-$^{19}F$ coupling constant of about 5 Hz. Deuterium atoms are preferable at the positions shown to avoid splitting of the fluorine signal.

Viewed from a further aspect the invention provides a physiologically tolerable MR imaging contrast agent comprising a compound selected from those—described above together with one or more physiologically tolerable carriers or excipients.

Viewed from a still further aspect the invention provides the use of a compound selected from those described above for the manufacture of an MR imaging agent for use in a method of diagnosis involving the generation of an MR image by MR imaging of a human or non-human body.

Viewed from a yet still further aspect the invention provides the use of a compound selected from those described above for the magnetic resonance imaging of a non-human, non-animal sample.

FIG. 1 of the accompanying drawings shows a typical $^{19}$F spectrum from molecule (I) following $^{15}$N-$^{19}$F polarisation transfer. In this case the polarisation transfer was 100%, the pulse sequence used was refocussed INEPT and the detection magnetic field had a strength of 1.5T.

By "physiologically tolerable solvent" we mean any solvent, solvent mixture or solution that is tolerated by the human or non-human animal body, e.g. water, aqueous solutions such as saline or aqueous alkanolic solutions, perfluorocarbons, etc. For in vivo imaging, the MR imaging agent should of course be physiologically tolerable or be capable of being presented in a physiologically tolerable form.

The MR imaging agent should preferably be strongly nuclear spin polarisable (for example, to a level of greater than 5%, preferably greater than 10%, more preferably greater than 25%) and have a low gyromagnetic ratio nuclei with a long T1 relaxation time under physiological conditions, e.g. $^{13}$C or $^{15}$N. By a long T1 relaxation time is meant that $T_1$ is such that once nuclear spin polarised, the MR imaging agent will remain so for a period sufficiently long to allow the imaging procedure to be carried out in a comfortable time span. Significant polarisation should therefore be retained for at least 5 s, preferably for at least 10 s, more preferably for at least 30 s, especially preferably at least 70 s, most especially preferably loos or longer.

The MR imaging agent should preferably be relatively small (e.g. molecular weight less than 5OOD, more preferably less than 300D (e.g. 50-300D) and more preferably 100 to 200D) and also preferably should be soluble in a liquid solvent or solvent mixture, most preferably in water or another physiologically tolerable solvent or solvent mixture. Furthermore, the chemical shift, or even better the coupling constant of the nmr signal from the imaging nucleus in the MR imaging agent should preferably be influenced by physiological parameters (e.g. morphology, pH, metabolism, temperature, oxygen tension, calcium concentration, etc). For example, influence by pH can be used as a general disease marker, whilst influence by metabolism may be a cancer marker. Alternatively, the MR imaging agent may conveniently be a material which is transformed (e.g. at a rate such that its half life is no more than $10 \times T_1$ of the reporter nucleus, preferably no more than $1 \times T_1$) in the subject under study to a material in which the MR imaging nucleus has a different coupling constant or chemical shift. In this case the subject may be inanimate or animate, e.g. a human or animal, a cell culture, a membrane- free culture, a chemical reaction medium, etc. Thus for example the reporter nucleus may provide information on the operation of the biochemical machinery of an organism where that machinery transforms the MR imaging agent and in so doing changes the chemical shift or coupling constant of the reporter nucleus. It will be appreciated that the imaging process used in this case may be an nmr spectroscopic procedure rather than (or in addition to) an imaging procedure which generates a morphological image.

Preferred MR imaging agents also exhibit the property of low toxicity.

Where the MR imaging nuclei is other than a proton, there will be essentially no interference from background signals if the natural abundance of the MR imaging nuclei is negligible and image contrast will be advantageously high. This is especially true where the MR imaging agent itself is enriched above natural abundance in the MR imaging nucleus, i.e. the higher gyromagnetic ratio nucleus. Thus the method according to the invention has the benefit of being able to provide significant spatial weighting to a generated image. In effect, the administration of a polarised MR imaging agent to a selected region of a sample (e.g. by injection) means that the contrast effect may be localised to that region. The precise effect of course depends on the extent of biodistribution over the period in which the MR imaging agent remains significantly polarised. In general, specific body volumes (i.e. regions of interest such as the vascular system, in particular the heart, or specific organs such as the brain, kidney or liver) into which the agent is administered may be defined with improved signal to noise (particularly improved contrast to noise) properties of the resulting images in these volumes.

In one embodiment, a "native image" of the sample (e.g. body) (i.e. one obtained prior to administration of the MR imaging agent or one obtained for the administered MR imaging agent without prior polarisation transfer as in a conventional MR experiment) may be generated to provide structural (e.g. anatomical) information upon which the image obtained in the method according to the invention may be superimposed.

Conveniently, the MR imaging agent once polarised will remain so for a period sufficiently long to allow the imaging procedure to be carried out in a comfortable time span. Generally sufficient polarisation will be retained by the MR imaging agent in its administrable form (e.g. in injection solution) if it has a $T_1$ value (at a field strength of 0.01-5T and a temperature in the range 20-40° C.) of at least 5 s, more preferably at least 10 s, especially preferably 30 s or longer, more especially preferably 70 s or more, yet more especially preferably 100 s or more (for example at 37° C. in water at 1T and a concentration of at least 1mM). The MR imaging agent may be advantageously an agent with a long $T_2$ relaxation time.

Given that the method of the invention should be carried out within the time that the MR imaging agent remains significantly polarised, once nuclear spin polarisation and dissolution has occurred, it is desirable for administration of the MR imaging agent to be effected rapidly and for the MR measurement to follow shortly thereafter. This means that the sample (e.g. body or organ) should be available close to the area in which the polarisation has been carried out. If this is not possible, he material should be transported to the relevant area, preferably at low temperature.

The long $T_1$ relaxation time of certain $^{13}$C and $^{15}$N nuclei is particularly advantageous and certain MR imaging agents containing $^{13}$C or $^{15}$N nuclei as the low gyromagnetic ratio nuclei are therefore preferred for use in the present method. Preferably the polarised MR imaging agent has an effective $^{13}$C nuclear polarisation of more than 0.1%, more preferably more than 1%, even more preferably more than 10%, particularly preferably more than 25%, especially preferably more than 50% and most especially preferably more than 95%.

For in vivo use, a polarised solid MR imaging agent may be dissolved in administrable media (e.g. water or saline), administered to a subject and conventional MR imaging performed. Thus solid MR imaging agents are preferably rapidly soluble (e.g. water soluble) to assist in formulating administrable media. Preferably the MR imaging agent should dissolve in a physiologically tolerable carrier (e.g. water or Ringers solution) to a concentration of at least 1 mM at a rate of 1 mM/$3T_1$ or more, particularly preferably 1 mM/$2T_1$, or more, especially preferably 1 mM/$T_1$ or more. Where the solid MR imaging agent is frozen, the administrable medium may be heated, preferably to an extent such that the temperature of the medium after mixing is close to 37° C.

Unless the polarised MR imaging agent is stored (and/or transported) at low temperature and in an applied field, since the method of the invention should be carried out within the time that the polarised solution of the MR imaging agent remains significantly polarised, it is desirable for administration of the polarised MR imaging agent to be effected rapidly and for the MR measurement to follow shortly thereafter. The preferred administration route for the polarised MR imaging agent is parenteral e.g. by bolus injection, by intravenous, intraarterial or peroral injection. The injection time should be equivalent to $5T_1$ or less, preferably $3T_1$ or less, more preferably $T_1$ or less, especially $0.1T_1$ or less. The lungs may be imaged by spray, e.g. by aerosol spray.

As stated previously, the MR imaging agent should be preferably enriched with nuclei (e.g. $^{15}N$ or $^{13}C$ nuclei) having a long $T_1$ relaxation time. Preferred are $^{13}C$ enriched MR imaging agents having $^{13}C$ at one particular position (or more than one particular position) in an amount in excess of the natural abundance, i.e. above about 1%. Preferably such a single carbon position will have 5% or more $^{13}C$, particularly preferably 10% or more, especially preferably 25% or more, more especially preferably 50% or more, even more preferably in excess of 99% (e.g. 99.9%). The $^{13}C$ nuclei should preferably amount to >2% of all carbon atoms in the compound. The MR imaging agent is preferably $^{13}C$ enriched at one or more carbonyl or quaternary carbon positions, given that a $^{13}C$ nucleus in a carbonyl group or in certain quaternary carbons may have a $T_1$ relaxation time typically of more than 2 s, preferably more than 5 s, especially preferably more than 30 s. Preferably the $^{13}C$ enriched compound should be deuterium labelled, especially adjacent the $^{13}C$ nucleus.

Preferred $^{13}C$ enriched compounds are those in which the $^{13}C$ nucleus is surrounded by one or more non-MR active nuclei such as 0, S, C or a double bond.

Also preferred are the following types of compound— (further details can be found in WO 99/35508 and WO 96/09282 which are herein incorporated by reference):
(1) carboxyl compounds comprising 1 to 4 carboxyl groups,
(2) substituted mono and biaryl compounds,
(3) sugars,
(4) ketones,
(5) ureas,
(6) amides,
(7) amino acids,
(8) carbonates.,
(9) nucleotides, and
(10) tracers.

The MR imaging agent should of course be physiologically tolerable or be capable of being provided in a physiologically tolerable, administrable form where the sample is animate.

Preferred MR imaging agents are soluble in aqueous media (e.g. water) and are of course non-toxic where the intended end use is in vivo.

The MR imaging agent may be conveniently formulated with conventional pharmaceutical or veterinary carriers or excipients. MR imaging agent formulations manufactured or used according to this invention may contain, besides the MR imaging agent, formulation aids such as are conventional for therapeutic and diagnostic compositions in human or veterinary medicine but will be clean, sterile and free of paramagnetic, superparamagnetic, ferromagnetic or ferrimagnetic contaminants. Thus the formulation may for example include stabilizers, antioxidants, osmolality adjusting agents, solubilizing agents, emulsifiers, viscosity enhancers, buffers, etc. Preferably none of such formulation aids will be paramagnetic, superparamagnetic, ferromagnetic or ferrimagnetic. The formulation may be in forms suitable for parenteral (e.g. intravenous or intraarterial) or enteral (e.g. oral or rectal) application, for example for application directly into body cavities having external voidance ducts (such as the lungs, the gastrointestinal tract, the bladder and the uterus), or for injection or infusion into the cardiovascular system. However solutions, suspensions and dispersions in physiological tolerable carriers (e.g. water) will generally be preferred.

Parenterally administrable forms should have low osmolality to minimize irritation or other adverse effects upon administration and thus the formulation should preferaly be isotonic or slightly hypertonic. Suitable vehicles include aqueous vehicles customarily used for administering parenteral solutions such as Sodium Chloride solution, Ringer's solution, Dextrose solution, Dextrose and Sodium Chloride solution, Lactated Ringer's solution and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the MR imaging agents and which will not interfere with the manufacture, storage or use of the products.

Where the MR imaging agent is to be injected, it may be convenient to inject simultaneously at a series of administration sites such that a greater proportion of the vascular tree may be visualized before the polarisation is lost through relaxation. Intra-arterial injection is useful for preparing angiograms and intravenous injection for imaging larger arteries and the vascular tree.

For use in in vivo imaging, the formulation, which preferably will be substantially isotonic, may conveniently be administered at a concentration sufficient to yield a 1 micromolar to 1M concentration of the MR imaging agent in the imaging zone; however the precise concentration and dosage will of course depend upon a range of factors such as toxicity, the organ targeting ability of the MR imaging agent, and the administration route. The optimum concentration for the MR imaging agent represents a balance between-various factors. In general, optimum concentrations would in most cases lie in the range 0.1 mM to 10M, especially 0.2 mM to 1M, more especially 0.5 to 500 mM. Formulations for intravenous or intraarterial administration would preferably conain the MR imaging agent in concentrations of 10 mM to 10M, especially 50 mM to 500 mM. For bolus injection the concentration may conveniently be 0.1 mM to 10M, preferably 0.2 mM to 10M, more preferably 0.5 mM to 1M, still more preferably 1.0 mM to 500 mM, yet still more preferably 10 mM to 300 mM.

The dosages of the MR imaging agent used according to the method of the present invention will vary according to the precise nature of the MR imaging agents used, of the tissue or organ of interest and of the measuring apparatus. Preferably the dosage should be kept as low as possible whilst still achieving a detectable contrast effect. Typically the dosage will be approximately 10% of $LD_{50}$, eg in the range 1 to 1000 mg/kg, preferably 2 to 500 mg/kg, especially 3 to 300 mg/kg.

The contents of all publications referred to herein are incorporated by reference.

The invention claimed is:

1. A method of magnetic resonance investigation of a sample, preferably a human or non-human animal body, said method comprising:
   i) obtaining a MR imaging agent containing in its molecular structure at least one storage and one detection non-zero nuclear spin nuclei of different gyromagnetic ratio values wherein said storage and said detection nuclei are present within the same molecule and wherein said storage and said detection nuclei are separated by 2 up to 5 chemical bonds;
   ii) nuclear spin polarising said storage nuclei in said MR imaging agent;
   iii) administering the polarised MR imaging agent to said sample;
   iv) subjecting said sample to a pulse sequence which causes polarisation to be transferred from said storage nuclei to at least one detection non- zero nuclear spin nuclei, wherein the gyromagnetic ratio of said detection nuclei is greater than that of said storage nuclei;
   v) exposing said sample to a radiation at a frequency selected to excite nuclear spin transitions in selected detection nuclei therein;
   vi) detecting magnetic resonance signals from said sample; and
   vii) optionally generating an image, dynamic flow data, diffusion data, perfusion data, physiological data or metabolic data from said detected signals.

2. The method as claimed in claim 1 wherein said method is used for angiography.

3. The method as claimed in claim 1 wherein said method is used for any fluid dynamic investigations of vascular system.

4. The method as claimed in claim 1 wherein said storage nuclei are selected from the group consisting of $^3$Li, $^{13}$C, $^{15}$N, $^{29}$Si and $^{77}$Sc nuclei.

5. The method as claimed in claim 4 wherein said storage nuclei are selected from the group consisting of $^{13}$C and $^{15}$N nuclei.

6. The method as claimed in claim 1 wherein said detection nuclei are selected from the group consisting of $^1$H, $^{19}$F or $^{31}$P nuclei.

7. The method as claimed in claim 6 wherein said detection nuclei are $^{19}$F nuclei.

8. The method as claimed in claim 1, wherein said storage nuclei are $^{15}$N nuclei and said detection nuclei are $^{19}$F nuclei.

9. The method as claimed in claim 1, wherein said gyromagnetic ratio of said detection nuclei is at least 25% higher than said gyromagnetic ratio of said storage nuclei.

10. The method as claimed in claim 9 wherein said gyromagnetic ratio of said detection nuclei is at least ten times higher than said gyromagnetic ratio of said storage nuclei.

11. The method as claimed in claim 1, wherein said polarisation transfer takes place with at least 75% efficiency.

12. The method as claimed in claim 11 wherein said efficiency is about 100% efficiency.

13. The method as claimed in claim 1 wherein said storage and detection nuclei are separated by 3 chemical bonds.

14. The method as claimed claim in 13 wherein the intervening nuclei between said storage and detection nuclei are I=0 nuclei and in their normal isotopic occurrence and if substituted, are substituted by I=0 nuclei or deuterium nuclei.

15. The method as claimed in claim 1, wherein said agent is water soluble.

16. The method as claimed in claim 1, wherein the efficiency of the polarisation transfer is dependent on the pH, oxygen tension, temperature or some other physiological parameter, allowing maps of said parameters to be constructed.

* * * * *